United States Patent [19]

Lewis et al.

[11] Patent Number: 5,157,175
[45] Date of Patent: Oct. 20, 1992

[54] COMPOSITION AND METHOD FOR INHIBITION OF STYRENE POLYMERIZATION

[75] Inventors: Vincent E. Lewis, Missouri City; Porcia E. West, Houston, both of Tex.

[73] Assignee: Nalco Chemical Company, Naperville, Ill.

[21] Appl. No.: 767,395

[22] Filed: Sep. 9, 1991

[51] Int. Cl.$^5$ .............................................. C07C 7/20
[52] U.S. Cl. ................................................ 585/5; 585/3
[58] Field of Search .................................... 585/5, 3

[56] References Cited

U.S. PATENT DOCUMENTS

| | | | |
|---|---|---|---|
| 3,390,198 | 6/1968 | Leston | 585/3 |
| 4,061,545 | 12/1977 | Watson | 203/9 |
| 4,177,110 | 12/1979 | Watson | 203/9 |
| 4,425,223 | 1/1984 | Miller | 208/48 AA |
| 4,439,278 | 3/1984 | Douglas et al. | 203/9 |
| 4,654,450 | 3/1987 | Miller | 585/5 |
| 4,654,451 | 3/1987 | Miller et al. | 585/5 |
| 4,692,544 | 9/1987 | Goerner et al. | 560/4 |
| 4,915,873 | 4/1990 | Abruscato et al. | 252/402 |
| 4,929,778 | 5/1990 | Roling | 585/3 |
| 4,967,027 | 10/1990 | Takahashi et al. | 585/5 |

FOREIGN PATENT DOCUMENTS 0162769  5/1952  Australia ............................... a/

Primary Examiner—Asok Pal
Assistant Examiner—P. Achutamurthy
Attorney, Agent, or Firm—Arnold, White & Durkee

[57] ABSTRACT

Polymerization of aromatic, ethylenically unsaturated monomers, such as styrene, is inhibited by adding alkyl phenol sulfonic acids.

10 Claims, 2 Drawing Sheets

COMPOSITION AND METHOD FOR INHIBITION OF STYRENE POLYMERIZATION

BACKGROUND OF THE INVENTION

1. Field of the Invention

The present invention relates to compositions comprising alkyl phenol sulfonic acids and to methods for inhibiting undesired polymerization of aromatic ethylenically unsaturated monomers using alkyl phenol sulfonic acids.

2. Background

Aromatic ethylenically unsaturated monomers, such as styrene ($C_6H_5CH=CH_2$), are used extensively for the manufacture of plastics. These monomers undergo undesirable thermal and free radical polymerization during storage, shipping, and particularly during processing. Such polymerization can cause fouling of distillation columns and other equipment used for processing the monomers and can render the monomers unfit for use without further treatment. To minimize polymerization, it is common practice to add to the monomer recovery stream, compounds which have polymerization inhibiting activity.

A wide variety of compounds have been used as polymerization inhibitors. U.S. Pat. No. 4,654,450, issued to Miller, discloses use of mixtures of dialkylhydroxylamines and alkyl benzene sulfonic acids as polymerization inhibitors. U.S. Pat. No. 4,425,223, issued to Miller, discloses use of mixtures of alkyl benzene sulfonic acids and alkyl esters of phosphonic acid to protect hydrocarbon processing equipment against fouling. U.S. Pat. Nos. 4,061,545 and 4,177,110, issued to Watson, disclose use of a mixture of tertiary-butylcatechol and phenothiazine as a polymerization inhibitor for vinyl aromatic compounds. U.S. Pat. No. 3,390,198, issued to Leston, discloses use of mono and dialkylcatechols as polymerization inhibitors for hot styrene.

Styrene manufacturers go to great lengths to remove air from the product recovery section of their plants. Thus, a polymerization inhibitor must work in the absence of oxygen. Current industry polymerization inhibitors include 2,4- and 2,6-dinitrophenol, plus alkylated homologues such as 2,4-dinitro-o-cresol and 2,4-dinitro-sec-butylphenol.

All of these products suffer from a common problem, toxicity. For example, $LD_{50}$ for 2,4-dinitrophenol is 30 mg/kg when administered to the interperitoneal cavity of a rat. In addition, both the dinitrophenols and dinitro-o-cresol have very low solubility, less than 5%, in either styrene or its precursor ethylbenzene. Companies that use either of these two products typically make up solutions in hot styrene or ethylbenzene. This provides increased solubility, however, the companies are then dealing with a known toxin dissolved in a hot carcinogen. Solubility problems can be overcome by using products such as dinitro-sec-butylphenol. The alkyl group does not add any activity to the product, however, so, while solubility in hydrocarbons is increased, product activity in terms of activity per pound is decreased.

It has now been discovered that alkyl phenol sulfonic acids provide outstanding polymerization inhibiting activity for aromatic ethylenically unsaturated monomers.

SUMMARY OF THE INVENTION

The present invention relates to compositions and methods for inhibition of polymerization of aromatic, ethylenically unsaturated monomers, and more particularly to the inhibition of styrene polymerization, using alkyl phenol sulfonic acids. The alkyl group of the alkyl phenol sulfonic acid polymerization inhibitors preferably contains from 1 to 10 carbon atoms, and more preferably contains nine carbon atoms. The alkyl phenol sulfonic acid polymerization inhibitor may be added to a monomer recovery stream by any conventional method and effectively inhibits polymerization when added in amounts in the range of about 300 to 900 ppm based on the weight of the monomer being treated.

BRIEF DESCRIPTION OF THE DRAWINGS

FIG. 4 illustrates the chemical structures of nonylphenol sulfonic acid and of other sulfonated products tested.

DETAILED DESCRIPTION OF THE INVENTION

Figure 1:
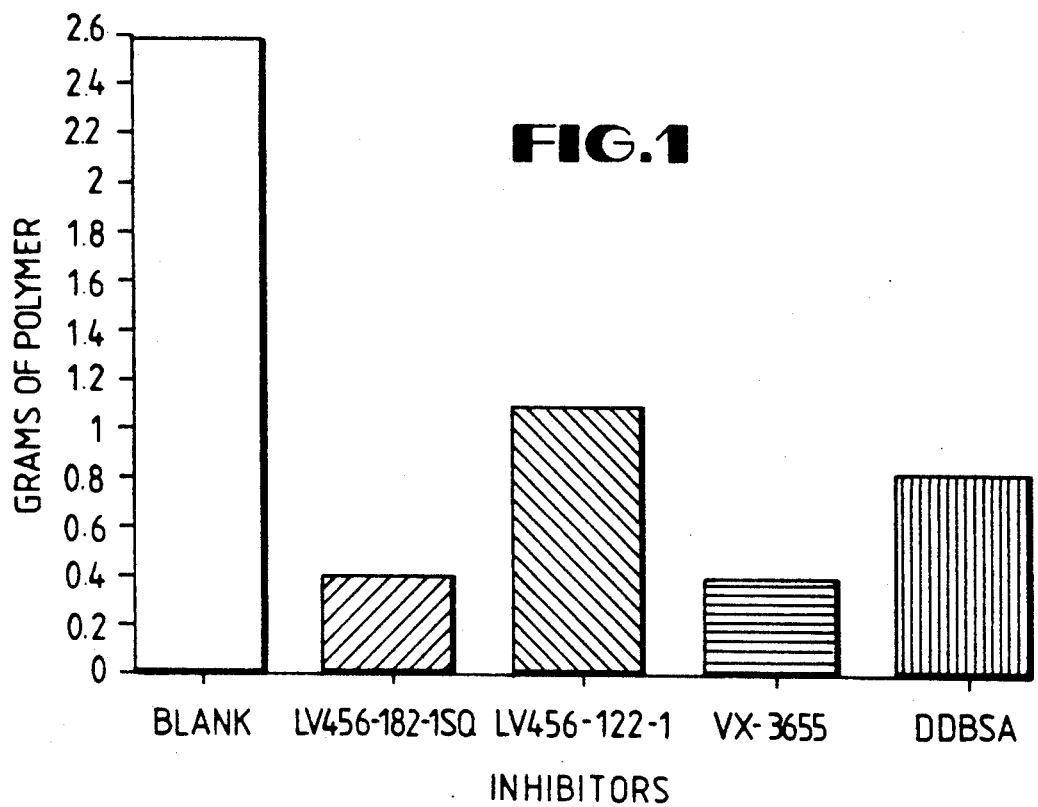
FIG. 1 illustrates the superiority of nonylphenol sulfonic acid as a styrene polymerization inhibitor. The figure compares sulfated nonylphenol resin, designated by LV456-182-1, nonylphenol sulphonic acid, designated by LV456-122-1, 4-hydroxybenzene sulphonic acid, designated by VX-3655, and dodecylbenzene sulfonic acid, designated by DDBSA.

The term "aromatic ethylenically unsaturated monomer," as used in this description, includes any of the readily polymerizable vinyl aromatic compounds, e.g., styrene, alpha alkyl styrene, ring alkyl substituted styrene, diethylenically substituted benzene compounds, and mixtures thereof.

The alkyl phenol sulfonic acids useful in the invention are those having the structural formula illustrated in FIG. 4 for nonylphenol sulfonic acid, wherein the alkyl group indicated by $C_9$ is an alkyl group that contains 1 or more carbon atoms. Preferred alkyl groups are those in which the total number of carbon atoms in the alkyl group is 1 to 10. Phenol sulfonic acid, i.e., 4-hydroxybenzene sulfonic acid, is soluble in water and only about 65% active. When styrene is dosed with this product, a second phase is formed. Nonylphenol sulfonic acid, however, is 100% active and completely soluble in styrene and, thus, is the preferred compound for use in this invention.

For the tests described herein, nonylphenol was sulfonated/sulfated using sulfur trioxide. The molar ratio of $SO_3$ to phenol ranged from 0.81 to 2.0. The reaction was carried out utilizing a laboratory sulfonation unit. This unit consisted of a glass thin-film falling reactor, a dual syringe pump for metering SO₃, and a gear pump for delivery of organic acceptors (nonylphenol in this case). Reactor and associated glassware temperature was controlled using circulating water baths. The resultant product was analyzed for degree of sulfonation/sulfation by titration with cyclohexylamine.

The polymerization inhibitor compositions of the invention can be introduced into the monomer to be protected by any conventional method. The polymerization inhibitor is used at a concentration which is effective to provide the desired protection against spontaneous polymerization. It has been determined that amounts of polymerization inhibitor in the range of about 300 to 900 ppm based on the weight of the monomer being treated are effective to inhibit polymerization.

The effectiveness of alkyl phenol sulfonic acids and of several other sulfonated or sulfated compounds as polymerization inhibitors has been evaluated by static testing. The static testing was performed as follows:

A 1000 mL aliquot of styrene was washed five times with 200 mL aliquots of water to remove 4-t-butylphenol, added as an antioxidant. The washed styrene was dried over sodium sulfate and then kept refrigerated until required for testing.

A ten mL aliquot of uninhibited styrene was placed in a 20 mL scintillation vial and dosed with the appropriate antipolymerant. A rubber septum was inserted into the vial and wired in place. An argon line was inserted into the septum, along with a vent needle, and argon was bubbled through the styrene for one minute. This was done to remove oxygen from the system. The vial was placed into an oven and heated for three hours at 225° F. The vial and septum were removed, and the contents diluted with a non-solvent. For this experiment, methanol was used. Since styrene is soluble in methanol, but polystyrene is not, polystyrene precipitated from the methanol solution. Polymer could thus be isolated and weighed. Comparison to the weight of polymer formed in an untreated sample provided the data for FIGS. 1-4.

During the polymerization over time study, aliquots of styrene were removed from the oven at 20 minute intervals. The rest of the experiment was conducted as described above.

In FIG. 1, the effectiveness of four sulfonated or sulfated products as a styrene polymerization inhibitor is compared to an untreated sample. Each of these products was dosed at 300 ppm based on the weight of the styrene monomer being treated. Sulfated nonylphenol resin (formed by the reaction of chlorosulfonic acid and nonylphenol/formaldehyde resin) and dodecylbenzene sulfonic acid (DDBSA) provided just over 50% inhibition as compared to an untreated styrene sample. Nonylphenol sulfonic acid and 4-hydroxybenzene sulfonic acid provided 85% inhibition as compared to an untreated sample.

Figure 2:
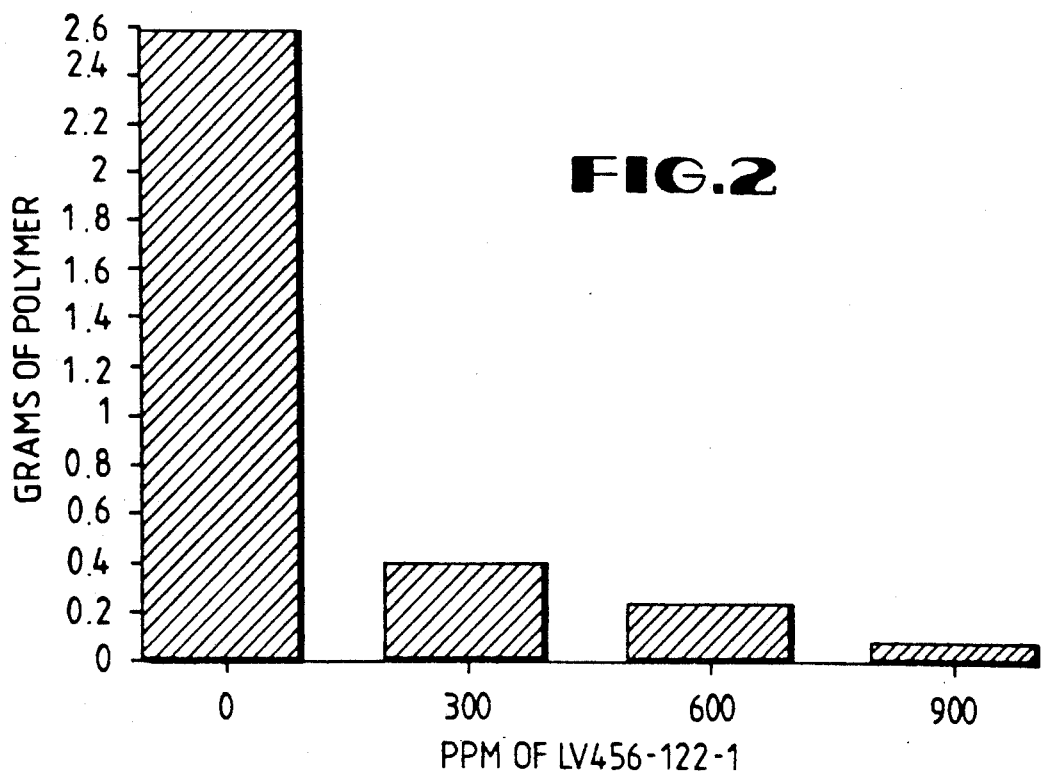
FIG. 2 illustrates the effectiveness of nonylphenol sulfonic acid designated as LV456-122-1, as a styrene polymerization inhibitor at different concentrations.

In FIG. 2, the effectiveness of nonylphenol sulfonic acid at different dosage levels was compared. At 900 ppm, nonylphenol sulfonic acid provided 98% inhibition of polymer formation.

Figure 3:
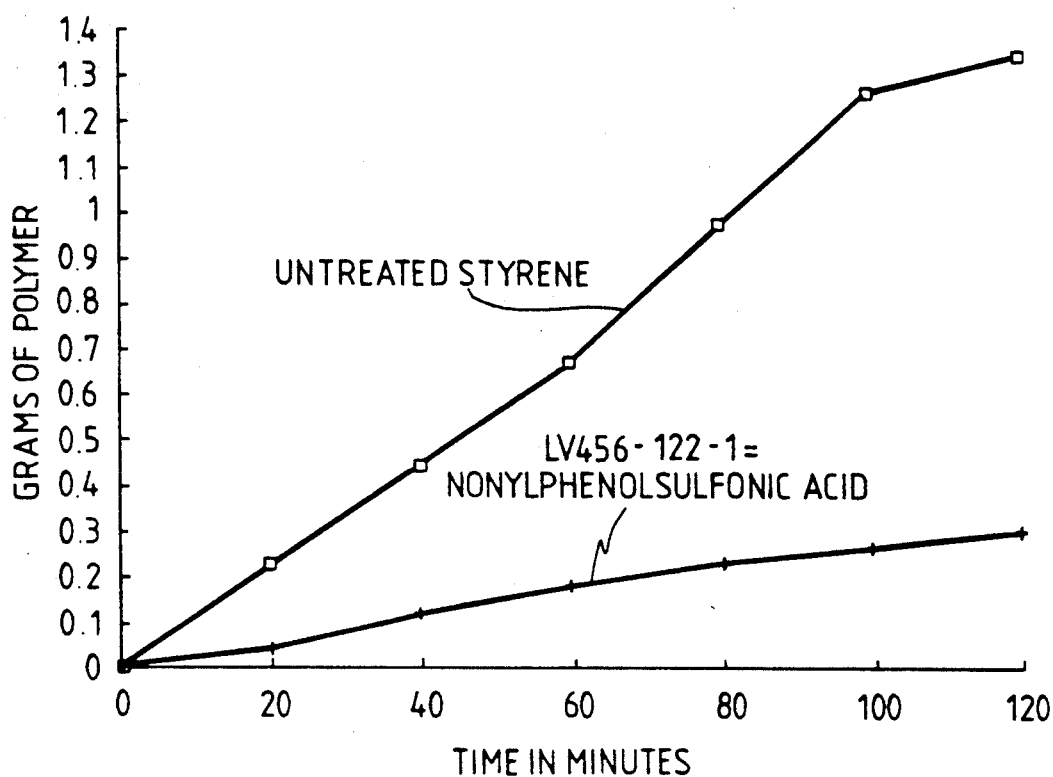
FIG. 3 compares the reduction in styrene polymer buildup over time in systems containing nonylphenol sulfonic acid and untreated systems.
Figure 4A:
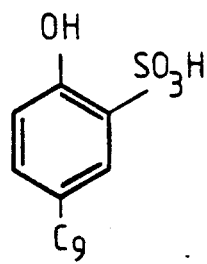
FIG. 4a is the chemical structure of nonylphenol sulfonic acid.
Figure 4B:
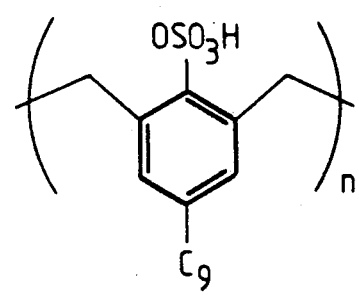
FIG. 4b is the chemical structure of sulfated nonylphenol resin.
Figure 4C:
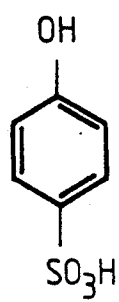
FIG. 4c is the chemical structure of the 4-hydroxybenzene sulfonic acid.
Figure 4D:
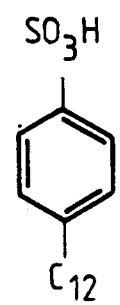
FIG. 4d is the chemical structure of dodecylbenzene sulphonic acid.

In FIG. 3, polymer buildup in styrene samples treated with nonylphenol sulfonic acid at a dosage level of 600 ppm was compared to polymer buildup in untreated styrene samples. The results of this study demonstrate that nonylphenol sulfonic acid retards styrene polymerization.

The two sulfated/sulfonated products which were least effective as styrene polymerization inhibitors were sulfated nonylphenol resin and dodecylbenzene sulfonic acid (DDBSA). In these two products, the active site is the acidic hydrogen atom. Both phenol sulfonic acids, nonylphenol sulfonic acid and 4-hydroxybenzene sulfonic acid, were more effective as polymerization inhibitors. The active sites for these products are the phenolic hydrogen atom and the sulfonic acid hydrogen. The radical formed when the phenol hydrogen is abstracted has added stability because it can be delocalized not only into the benzene ring, but also into the sulfonate group. Additionally, sulfur does not react with radicals easily, therefore, the sulfonate group is not easily destroyed by unwanted side reactions.

Although the present invention is described with particular reference to specific tests set forth above, it is understood that the invention includes obvious variants. For example, alkyl phenol sulfonic acids other than nonylphenol sulfonic acid can be used in the invention and the inhibitor composition can be formulated to contain more than one member of this group of compounds. The scope of the invention is limited only by the breadth of the appended claims.

What is claimed is:

1. A composition comprising aromatic, ethylenically unsaturated monomers and an amount effective to inhibit polymerization of said monomers of alkyl phenol sulfonic acid.

2. The composition of claim 1 wherein the alkyl group of said alkyl phenol sulfonic acid contains from 1 to 10 carbon atoms.

3. The composition of claim 2 wherein the alkyl group contains 9 carbon atoms.

4. The composition of claim 1 wherein the alkyl phenol sulfonic acid is present in an amount of about 300 to 900 ppm based on the weight of the monomer being treated.

5. The composition of claim 1 wherein said aromatic, ethylenically unsaturated monomer is styrene and said alkyl phenol sulfonic acid is nonylphenol sulfonic acid, and wherein said nonylphenol sulfonic acid is present in an amount of about 300 to 900 ppm based on the weight of the styrene monomer being treated.

6. A method of inhibiting polymerization of aromatic, ethylenically unsaturated monomers comprising adding to the monomers an amount effective to inhibit polymerization of said monomers of alkyl phenol sulfonic acid.

7. The method of claim 6 wherein the alkyl group of said alkyl phenol sulfonic acid contains from 1 to 10 carbon atoms.

8. The method of claim 7 wherein the alkyl group contains carbon atoms.

9. The method of claim 6 wherein the alkyl phenol sulfonic acid is added to said monomer in an amount of about 300 to 900 ppm based on the weight of the monomer being treated.

10. The method of claim 6 wherein said aromatic, ethylenically unsaturated monomer is styrene and said alkyl phenol sulfonic acid is nonylphenol sulfonic acid, and wherein said nonylphenol sulfonic acid is added to the monomer in an amount of about 300 to 900 ppm based on the weight of the styrene monomer being treated.

* * * * *

UNITED STATES PATENT AND TRADEMARK OFFICE
CERTIFICATE OF CORRECTION

PATENT NO. : 5,157,175
DATED : October 20, 1992
INVENTOR(S) : Vincent E. Lewis and Porcia E. West It is certified that error appears in the above-indentified patent and that said Letters Patent is hereby corrected as shown below:

Column 4, Claim 8, line 2, insert —9— before "carbon atoms"

Signed and Sealed this

Twelfth Day of October, 1993

Attest:

BRUCE LEHMAN

Attesting Officer

Commissioner of Patents and Trademarks